(12) United States Patent
O'Brien et al.

(10) Patent No.: US 11,596,417 B2
(45) Date of Patent: Mar. 7, 2023

(54) HEMOSTASIS BAND WITH IMPROVED EDGE DESIGN

(71) Applicant: TERUMO KABUSHIKI KAISHA, Tokyo (JP)

(72) Inventors: Victoria Moore O'Brien, Sewell, NJ (US); Brian Hoffman, Princeton, NJ (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 18 days.

(21) Appl. No.: 16/288,303

(22) Filed: Feb. 28, 2019

(65) Prior Publication Data

US 2020/0275936 A1    Sep. 3, 2020

(51) Int. Cl.
*A61B 17/135* (2006.01)
*A61B 17/12* (2006.01)

(52) U.S. Cl.
CPC ........... *A61B 17/135* (2013.01); *A61B 2017/12004* (2013.01)

(58) Field of Classification Search
CPC ........ A61B 17/135; A61B 17/132; A61B 17/1322; A61B 17/1325; A61B 17/1327; A61B 17/1355; A61B 17/12; A61B 17/12009; A61B 17/12013; A61B 2017/12004; A61B 2017/12018; A61B 5/029; A61B 17/1324; A61B 5/6824; A41D 20/00; A61F 13/00; A61F 5/01; A61F 5/25–5/28; A61F 5/0009; A61F 2007/0228; A61F 2007/023; A61F 2007/0231; A61F 2007/0233; A61F 2013/00093; A61H 9/0092; A61H 2011/005; A61H 2201/1645; A63B 21/0085; A63B 21/4025; A44C 5/14; A44C 5/0053
USPC ................................ 606/201, 202; 601/149
See application file for complete search history.

(56) References Cited

U.S. PATENT DOCUMENTS

| | | | | |
|---|---|---|---|---|
| 1,763,929 | A | * | 6/1930 | Kellner ................. A45C 11/22 368/282 |
| 2,347,197 | A | | 4/1944 | La Liberte |
| 3,120,846 | A | | 2/1964 | Fletcher |
| 3,587,584 | A | | 6/1971 | Keller |

(Continued)

FOREIGN PATENT DOCUMENTS

| CN | 201987613 U | 9/2011 |
|---|---|---|
| EP | 1016379 A1 | 7/2000 |

(Continued)

OTHER PUBLICATIONS

International Search Report and Written Opinion of International Application No. PCT/US2020/017618, dated Jun. 22, 2020 (9 pages).

(Continued)

*Primary Examiner* — Kathleen S Holwerda
*Assistant Examiner* — Lauren Dubose
(74) *Attorney, Agent, or Firm* — Buchanan Ingersoll & Rooney PC (57) ABSTRACT

The present application discloses various embodiments of a hemostatic device with improved comfort features over the known prior art, including hemostatic devices having attachment straps with non-linear edges and/or non-planar skin-facing edges.

17 Claims, 4 Drawing Sheets

(56) References Cited

U.S. PATENT DOCUMENTS

| | | | |
|---|---|---|---|
| 3,670,735 A | 6/1972 | Hazlewood | |
| 4,466,159 A * | 8/1984 | Burrage | B65D 63/10 |
| | | | 24/16 PB |
| 4,637,394 A | 1/1987 | Racz et al. | |
| 5,312,431 A * | 5/1994 | McEwen | A61B 17/135 |
| | | | 606/202 |
| 6,506,206 B1 * | 1/2003 | Guzman | A61B 17/135 |
| | | | 606/203 |
| 6,592,535 B2 | 7/2003 | Ravikumar | |
| 7,498,477 B2 | 3/2009 | Wada et al. | |
| 9,271,738 B2 | 3/2016 | Ward et al. | |
| 9,332,994 B2 | 5/2016 | Pancholy et al. | |
| 9,427,239 B2 | 8/2016 | Benz et al. | |
| 2003/0229375 A1 * | 12/2003 | Fleischer | A61B 17/1325 |
| | | | 606/201 |
| 2008/0109937 A1 * | 5/2008 | Greer | G09F 3/005 |
| | | | 2/162 |
| 2012/0232578 A1 | 9/2012 | Altobelli et al. | |
| 2015/0018869 A1 | 1/2015 | Benz et al. | |
| 2016/0038154 A1 | 2/2016 | Cohen et al. | |
| 2017/0215892 A1 | 8/2017 | Pancholy | |
| 2017/0224357 A1 * | 8/2017 | Whalen | A61B 17/135 |
| 2018/0008281 A1 | 1/2018 | Hazama | |
| 2018/0008282 A1 | 1/2018 | Hazama et al. | |
| 2018/0008283 A1 | 1/2018 | Hazama | |
| 2018/0042615 A1 * | 2/2018 | Kimura | A61B 17/1325 |
| 2018/0185032 A1 | 7/2018 | Matsushita et al. | |
| 2019/0021742 A1 | 1/2019 | Hazama | |
| 2019/0111298 A1 * | 4/2019 | Whalen | A61H 9/0092 |

FOREIGN PATENT DOCUMENTS

| | | |
|---|---|---|
| EP | 2662034 B1 | 11/2017 |
| JP | 2002069724 A1 | 3/2002 |
| JP | 2005-318998 A | 11/2005 |
| JP | 2014-200308 A | 10/2014 |
| JP | 2017-047037 A | 3/2017 |
| KR | 101021608 B1 | 3/2011 |
| WO | 2014137302 A1 | 9/2014 |
| WO | 2017/039005 A1 | 3/2017 |

OTHER PUBLICATIONS

Medtronic TRAcelet Compression Device Technical Specifications, [online], [Retrieved on Nov. 2, 2018] Retrieved from the internet: <https://www.medtronic.com/content/dam/medtronic-com/us-en/hcp/therapies-conditions/transradial/documents/uc201704407en-tracelet-tech-specs.pdf>.

The extended European Search Report dated Oct. 24, 2022, by the European Patent Office in corresponding European Patent Application No. 20762470.1-1122. (10 pages).

* cited by examiner

HEMOSTASIS BAND WITH IMPROVED EDGE DESIGN

BACKGROUND

The present invention relates to a hemostasis band that is adapted to act as a compression device to promote hemostasis at a surgical access site, and more particularly to a hemostasis band having an improved edge design for increased user comfort.

After a surgical procedure involving arterial or venous access, it may be desirable or necessary to apply pressure to the access site to promote hemostasis. Some existing hemostasis bands may be uncomfortable to users. Accordingly, there is a need for a hemostasis band that addresses this and other drawbacks of the prior art.

SUMMARY OF THE DISCLOSURE

In one respect, the present disclosure comprises a hemostatic device comprising: a main body adapted to fit around at least a portion of a limb of a patient, the main body including at least one compression element adapted to apply pressure to at least one artery or vein located in the limb when the hemostatic device is attached around the at least a portion of the limb; a first attachment strap hingedly attached to the main body by a first flexible connector, the first attachment strap including a first fastener half, an interior side, and a perimeter, the perimeter being measured along a lateral edge of the first flexible connector and along a first side edge, an end edge, and a second side edge of the first attachment strap between a first point where the first side edge meets the first flexible connector and a second point where the second side edge meets the first flexible connector, the lateral edge of the first flexible connector being defined by a line drawn between the first point and the second point, the end edge including a first corner corresponding to where the end edge meets the first side edge and a second corner corresponding to where the end edge meets the second side edge; and a second attachment strap hingedly attached to the main body by a second flexible connector, the second attachment strap including a second fastener half that is attachable to the first fastener half such that the first attachment strap and second attachment strap are attachable together to hold the hemostatic device in place around the at least a portion of the limb, the second attachment strap further including an interior side and a perimeter, the perimeter of the second attachment strap being measured along a lateral edge of the second flexible connector and along a first side edge, an end edge, and a second side edge of the second attachment strap between a first point where the first side edge of the second attachment strap meets the second flexible connector and a second point where the second side edge of the second attachment strap meets the second flexible connector, the lateral edge of the second flexible connector being defined by a line drawn between the first point on the second attachment strap and the second point on the second attachment strap, the end edge of the second attachment strap including a first corner corresponding to where the end edge of the second attachment strap meets the first side edge thereof and a second corner corresponding to where the end edge of the second attachment strap meets the second side edge thereof; wherein each of the interior sides of the first attachment strap and the second attachment strap is bounded by its respective perimeter, and each of the interior sides of the first attachment strap and the second attachment strap is oriented towards the at least a portion of the limb when the hemostatic device is attached around the at least a portion of the limb; and wherein at least one of the first side edge of the first attachment strap, the second side edge of the first attachment strap, the first side edge of the second attachment strap, and the second side edge of the second attachment strap is non-linear, and/or at least one of the interior side of the first attachment strap and the interior side of the second attachment strap is non-planar when the hemostatic device is not attached around the at least a portion of the limb.

In another respect, the present disclosure comprises a hemostatic device comprising: a main body adapted to fit around at least a portion of a limb of a patient, the main body including at least one compression element adapted to apply pressure to at least one artery or vein located in the limb when the hemostatic device is attached around the at least a portion of the limb; a first attachment strap hingedly attached to the main body by a first flexible connector, the first attachment strap including a first fastener half and a perimeter, the perimeter being measured along a lateral edge of the first flexible connector and along a first side edge, an end edge, and a second side edge of the first attachment strap between a first point where the first side edge meets the first flexible connector and a second point where the second side edge meets the first flexible connector, the lateral edge of the first flexible connector being defined by a line drawn between the first point and the second point, the end edge including a first corner corresponding to where the end edge meets the first side edge and a second corner corresponding to where the end edge meets the second side edge; and a second attachment strap hingedly attached to the main body by a second flexible connector, the second attachment strap including a second fastener half that is attachable to the first fastener half such that the first attachment strap and second attachment strap are attachable together to hold the hemostatic device in place around the at least a portion of the limb, the second attachment strap further including a perimeter, the perimeter of the second attachment strap being measured along a lateral edge of the second flexible connector and along a first side edge, an end edge, and a second side edge of the second attachment strap between a first point where the first side edge of the second attachment strap meets the second flexible connector and a second point where the second side edge of the second attachment strap meets the second flexible connector, the lateral edge of the second flexible connector being defined by a line drawn between the first point on the second attachment strap and the second point on the second attachment strap, the end edge of the second attachment strap including a first corner corresponding to where the end edge of the second attachment strap meets the first side edge thereof and a second corner corresponding to where the end edge of the second attachment strap meets the second side edge thereof; wherein at least one of the first side edge of the first attachment strap, the second side edge of the first attachment strap, the first side edge of the second attachment strap, and the second side edge of the second attachment strap is non-linear.

In yet another respect, the present disclosure comprises a hemostatic device comprising a main body adapted to fit around at least a portion of a limb of a patient, the main body including at least one compression element adapted to apply pressure to at least one artery or vein located in the limb when the hemostatic device is attached around the at least a portion of the limb; a first attachment strap hingedly attached to the main body by a first flexible connector, the first attachment strap including a first fastener half and an interior side bounded by a perimeter, the perimeter being measured along a first side edge, an end edge, and a second side edge of the first attachment strap between a first point where the first side edge meets the first flexible connector and a second point where the second side edge meets the first flexible connector; and a second attachment strap hingedly attached to the main body by a second flexible connector, the second attachment strap including a second fastener half that is attachable to the first fastener half such that the first attachment strap and second attachment strap are attachable together to hold the hemostatic device in place around the at least a portion of the limb, the second attachment strap further including an interior side bounded by a perimeter, the perimeter of the second attachment strap being measured along a first side edge, an end edge, and a second side edge of the second attachment strap between a first point where the first side edge of the second attachment strap meets the second flexible connector and a second point where the second side edge of the second attachment strap meets the second flexible connector; wherein each of the interior sides of the first attachment strap and the second attachment strap is oriented towards the at least a portion of the limb when the hemostatic device is attached around the at least a portion of the limb; and wherein at least one of the interior side of the first attachment strap and the interior side of the second attachment strap is non-planar when the hemostatic device is not attached around the at least a portion of the limb.

BRIEF DESCRIPTION OF THE DRAWINGS

The present disclosure will hereinafter be described in conjunction with the appended drawing figures, wherein like numerals denote like elements.

DETAILED DESCRIPTION OF THE EMBODIMENT(S)

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features.

Peripheral vascular interventions are commonly used to attempt to clear occlusions from, or surgically introduce stents into, vascular pathways. For example, antegrade crossing via the radial artery in a patient's wrist is common, and various retrograde approaches upwardly from below a patient's knee are also established procedures. After such a procedure, the vascular (i.e., either arterial or venous) access site is typically closed through application of pressure to encourage hemostasis.

Hemostatic devices that are wrapped around a patient's limb at a site on the limb where bleeding is to be stopped, and which include one or more inflatable balloons or bladders that target pressure at a vascular access site, are known in the art. Multiple embodiments of one such hemostatic device and methods of using such devices are described in U.S. Pat. No. 7,498,477, the entirety of which is incorporated by reference as if set forth herein.

Such hemostasis bands are commonly annular or cuff-like in shape, having linear side edges and planar attachment strap portions (when not in use or subject to outside forces or deformation thereof). When secured around a patient's limb, the edges of these hemostatic devices may dig into the user's limb or otherwise become uncomfortable to the user because of stresses concentrated along the edges of the attachment straps. Thus, hemostasis bands having improved comfort designs are desirable.

Figure 1:
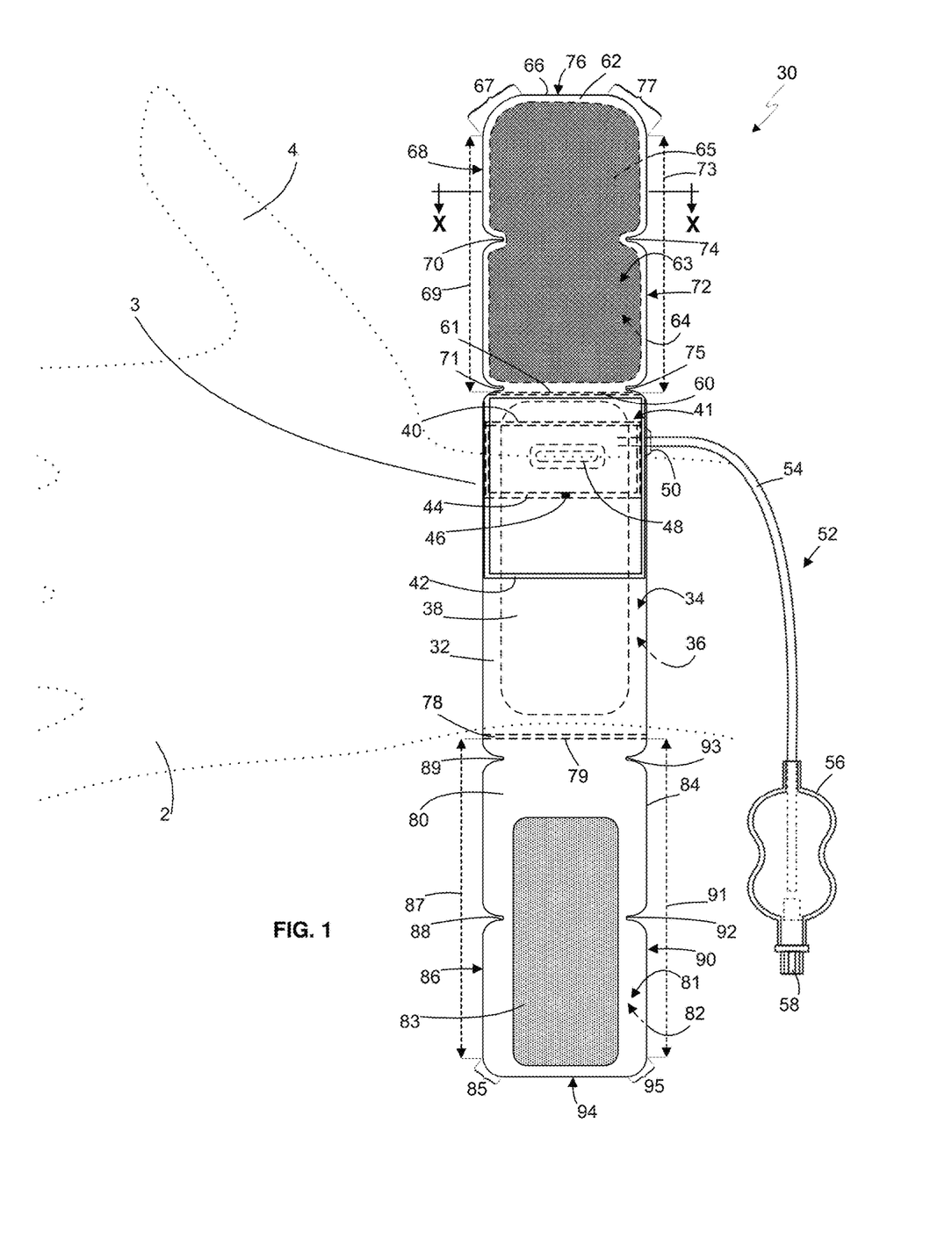
FIG. 1 is a top view of the interior side of a hemostasis band according to an embodiment of the present disclosure, in an unwrapped configuration.

Referring now to the Figures, various embodiments of hemostatic devices, in the form of hemostasis bands, will now be described in detail. FIG. 1 shows an embodiment of a hemostasis band 30 according to the present disclosure. In this embodiment, the hemostasis band 30 is designed to be wrapped and secured in place around a wrist 3 of a patient to encourage hemostasis of the radial artery, as would be understood by a person having ordinary skill in the art. In FIG. 1, portions of a left hand 2 and wrist 3 of a hypothetical patient are shown in phantom lines for discussion purposes, palm down (i.e., as if facing the page, with the wrist 3 facing the device). It should be understood that the concepts discussed in the present disclosure have applicability to other hemostatic devices that may be employed elsewhere on a patient's body, for example on any portion of any limb or the torso, neck, or head.

In FIG. 1, the hemostasis band 30 is shown in its undeployed or unwrapped state, lying flat on a planar surface. The hemostasis band 30 comprises a main body 32, an attachment strap 62 attached to the main body 32 by a flexible connector 60, and an attachment strap 80 attached to an opposing side of the main body 32 by a flexible connector 78. The main body 32 comprises an interior side 34 that is oriented towards (i.e., faces) the wrist 3 and an exterior side 36 that is oriented away from the wrist 3 when the hemostasis band 30 is attached thereto. In this embodiment, the hemostasis band 30 further comprises a curved plate 38 attached to the main body 32, the curved plate 38 adapted to wrap around at least a portion of the wrist 3 when the hemostasis band 30 is attached thereto, such that at least one compression element, as further discussed below, is located between the curved plate 38 and the at least one artery or vein where the access site is located. In this embodiment, the curved plate 38 is held in the hemostasis band 30 by being inserted between two layers of overlapping material (not separately labeled in FIG. 1) that comprise the main body 32 of the hemostasis band 30. Further, in this embodiment the curved plate 38 is comprised of a material that is more rigid than that of the hemostasis band 30 and is designed to maintain a substantially constant shape.

FIG. 1 also shows the compression element 41, which in this embodiment is provided with an inflatable dual-balloon configuration similar to the embodiments taught in U.S. Pat. No. 7,498,477. The dual pneumatic balloon design supports a process to titrate air and reduce compression (pressure) during recovery, which allows for the artery or vein to remain patent over time. In this embodiment, the compression element 41 is comprised of a main balloon 42, a secondary balloon 44, and a connector 40 which serves as a joining portion between the main body 32, the main balloon 42, and the secondary balloon 44. An opening 48 exists between an interior of the main balloon 42 and an interior of the secondary balloon 44, so that the secondary balloon 44 inflates as the main balloon 42 inflates, providing for efficient ease of use. In an alternate embodiment (not shown), the main balloon 42 and secondary balloon are each connected separately to the main body 32 via separate connectors, such that each balloon 42,44 has an individual hinge line with respect to the main body 32.

An air tube 54 enters the interior of the main balloon 42 via a port 50, and the air tube 54 is connected at its opposite end to an inflator 52. In this embodiment, the inflator 52 includes a bulb 56 and a valve housing 58. Inflation of the balloons 42,44 is achieved by inserting the protruding tip of a syringe (not shown) into the valve housing 58 and pushing a plunger on the syringe so as to introduce fluid (e.g., air) within the syringe through the inflator 52 into the balloons 42,44. Once fluid has been injected into the balloons 42,44 and the protruding tip of the syringe is withdrawn from the valve housing 58, a check valve (not shown) within the valve housing 58 closes, preventing the fluid from leaking out and thus maintaining the balloons 42,44 in an inflated state. In the present embodiment, when both balloons 42,44 are inflated, the secondary balloon 44 provides oblique pressure against the main balloon 42, which in turn provides targeted pressure to the vascular access site, thus promoting hemostasis. The curved plate 38—which, as noted above, is rigid—acts to direct the pressure created by the inflated balloons 42,44 towards the vascular access site, instead of permitting this pressure to displace or stretch the main body 32 of the hemostasis band 30 away from the vascular access site.

In this embodiment, the compression element 41 further includes a marker 46 located on an interior edge of the secondary balloon 44 (and approximately in the center of the main balloon 42), which permits the clinician to align the balloons 42,44 over the center of the vascular access site (in this embodiment, the radial artery located in the wrist 3). In alternate embodiments, the marker 46 could be placed on another surface of the hemostasis band 30, for example the center of the main balloon 42, the main body 32, or the curved plate 38, or the marker 46 could be omitted entirely.

In the present embodiment, the main body 32, all components of the compression element 41, and the attachment straps 62,80 are transparent to allow for visualization of the vascular access site and monitor for bleeding during the hemostasis period. Further, in the present embodiment, the hemostasis band 30 is comprised of polyvinyl chloride (PVC). In alternate embodiments, all or portions of the hemostasis band 30 could be formed from opaque materials and/or alternate types of materials. In further alternate embodiments, only the portions of the hemostasis band 30 that are to be located in the vicinity of the vascular access site could be formed from transparent materials, and the remainder of the hemostasis band 30 could be formed from opaque and/or semi-opaque materials. The hemostasis band 30 could also optionally be equipped with a patency monitoring sensor.

In additional alternate embodiments, the compression element 41 could be formed with only one balloon and/or balloon(s) of different sizes than the balloons 42,44 of the present embodiment. In further alternate embodiments the balloons could be omitted entirely, and the hemostatic pressure could be achieved via a material pad or a mechanical device that applies pressure to the desired vascular access site.

Turning back to the embodiment of FIG. 1, the attachment strap 62 comprises an interior side 63 that is oriented towards (i.e., faces) the wrist 3 and an exterior side 64 that is oriented away from the wrist 3 when the hemostasis band 30 is attached thereto, and a fastener half 65 that is located on the exterior side 64 thereof. Similarly, the attachment strap 80 comprises an interior side 81 that is oriented towards (i.e., faces) the wrist 3 and an exterior side 82 that is oriented away from the wrist 3 when the hemostasis band 30 is attached thereto, and a fastener half 83 that is located on the interior side 81 thereof. The fastener halves 65,83 are releasably attachable together so that the attachment straps 62,80 are releasably attachable together to hold the hemostasis band 30 in place around the patient's wrist 3. In alternate embodiments, the locations of the fastener halves 65,83 on the respective attachment straps 62,80 could be reversed, such that the inward-facing fastener half is attached to the radial (thumb 4) side of the hemostasis band 30.

In this embodiment, the fastener halves 65,83 are complementary patches of hook-and-loop type fasteners (e.g., Velcro®), and permit for the size (i.e., circumference) of the hemostasis band 30 to be adjusted for use on patients with a wide range of limb thickness. In alternate embodiments, the fastener halves 65,83 could be formed from any suitable type of fastener, for example snaps, buttons, laces, zippers, or hook-and-eyelet combinations.

In further alternate embodiments, the hemostasis band 30 according to the present disclosure could be formed with a single, long attachment strap and a strap loop mounted to the main body 32, wherein the single attachment strap could be routed through the strap loop and then releasably attached to itself via any known type of fastener.

Again turning back to the embodiment of FIG. 1, the attachment strap 62 further comprises a perimeter 66 that is measured along a lateral edge 61 of the flexible connector 60 and along a side edge 68, an end edge 76, and a side edge 72 of the attachment strap 62 between a first point (not labeled) where the side edge 68 meets the flexible connector 60 and a second point (not labeled) where the side edge 72 meets the flexible connector 60, the lateral edge 61 of the flexible connector 60 being defined by a line drawn between the first point and the second point, and the end edge 76 including a corner 67 corresponding to where the end edge 76 meets the side edge 68 and a corner 77 corresponding to where the end edge 76 meets the side edge 72. In this embodiment, the side edge 68 has a longitudinal length 69 measured in a straight line along the side edge 68 between the lateral edge 61 of the flexible connector 60 and the end edge 76, and further includes cutouts 70,71 along its linear length (i.e., along that portion of the perimeter 66 corresponding to the side edge 68). Due to the cutouts 70,71, the linear length of the side edge 68 is greater than the longitudinal length 69 thereof. Further, in this embodiment, the side edge 72 has a longitudinal length 73 measured in a straight line along the side edge 72 between the lateral edge 61 of the flexible connector 60 and the end edge 76, and further includes cutouts 74,75 along its linear length (i.e., along that portion of the perimeter 66 corresponding to the side edge 72). Due to the cutouts 74,75, the linear length of the side edge 72 is greater than the longitudinal length 73 thereof.

The attachment strap 80 further comprises a perimeter 84 that is measured along a lateral edge 79 of the flexible connector 78 and along a side edge 86, an end edge 94, and a side edge 90 of the attachment strap 80 between a first point (not labeled) where the side edge 86 meets the flexible connector 78 and a second point (not labeled) where the side edge 90 meets the flexible connector 78, the lateral edge 79 of the flexible connector 78 being defined by a line drawn between the first point and the second point, and the end edge 94 including a corner 85 corresponding to where the end edge 94 meets the side edge 86 and a corner 95 corresponding to where the end edge 94 meets the side edge 90. In this embodiment, the side edge 86 has a longitudinal length 87 measured in a straight line along the side edge 86 between the lateral edge 79 of the flexible connector 78 and the end edge 94, and further includes cutouts 88,89 along its linear length (i.e., along that portion of the perimeter 84 corresponding to the side edge 86). Due to the cutouts 88,89, the linear length of the side edge 86 is greater than the longitudinal length 87 thereof. Further, in this embodiment, the side edge 90 has a longitudinal length 91 measured in a straight line along the side edge 90 between the lateral edge 79 of the flexible connector 78 and the end edge 94, and further includes cutouts 92,93 along its linear length (i.e., along that portion of the perimeter 84 corresponding to the side edge 90). Due to the cutouts 92,93, the linear length of the side edge 90 is greater than the longitudinal length 91 thereof.

In the present embodiment the corners 67, 77, 85, 95 are each rounded (i.e., have a radius) for increased patient comfort. In alternate embodiments, any one or more of the corners 67, 77, 85, 95 could be chamfered, otherwise beveled, or could form a right angle.

The cutouts 70, 71, 74, 75, 88, 89, 92, 93 located in the side edges 68, 72, 86, 90 of the attachment straps 62,80—which in this embodiment permits the attachment straps 62,80 to be referred to as "scalloped"-shaped—act as flexible relief cuts in the side edges 68, 72, 86, 90 which interrupt and reduce the tension that is applied to the patient's wrist 3 during use as compared to hemostatic devices having linear edge constructions where stresses are concentrated more highly along the side edges thereof.

While, in the present embodiment, each of the four side edges 68, 72, 86, 90 of the attachment straps 62,80 includes two cutouts, in alternate embodiments a greater or lesser number of cutouts could be included in each of the side edges. In further alternate embodiments, the size and/or shape of each cutout could be different from those shown in FIG. 1, and cutouts of different sizes and shapes could be used on the same hemostatic device. In still further alternate embodiments, cutouts could also be included along the side edges of the main body 32 and/or some or all of the inflatable elements (e.g., main balloon 42 and/or secondary balloon 44).

The inventor(s) have conceived of still additional embodiments of attachment bands for hemostatic devices with improved edge designs and comfort features over the known prior art. FIGS. 2-7 show sectional views of various embodiments of an attachment strap for a hemostasis band taken along hypothetical sectional line X-X of FIG. 1. Said another way, FIGS. 2-7 do not show sectional views of the embodiment shown in FIG. 1, but instead show sectional views of an attachment strap according to various embodiments, taken along a line that would approximately correspond with line X-X if line X-X were overlaid on attachment straps of these additional embodiments.

Figure 2:
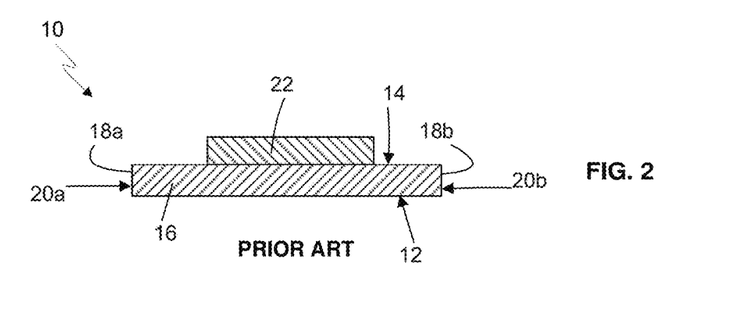
FIG. 2 is a sectional view of a hemostasis band according to the prior art, taken along a hypothetical section line similar to section line X-X of FIG. 1.

FIG. 2 is a sectional view of an attachment strap 10 for a hemostasis band according to the prior art, which is comprised of a piece 16 of material having side edges 18a,18b that correspond with the side edges 20a,20b of the attachment strap 10 that is formed by the piece 16. The attachment strap 10 according to this prior art embodiment comprises an interior side 12 that is oriented towards (i.e., faces) the wrist 3 and an exterior side 14 that is oriented away from the wrist 3 when the respective hemostasis band is attached thereto, with a fastener half 22 attached to the exterior side 14. In this prior art embodiment, the interior side 12 of the attachment strap 10 is planar to its side edges 20a,20b when the respective hemostatic device is not attached around the patient's limb (or otherwise subject to outside forces or non-typical deformations, e.g., accidental or intentional plastic deformations of the piece 16).

Figure 3:
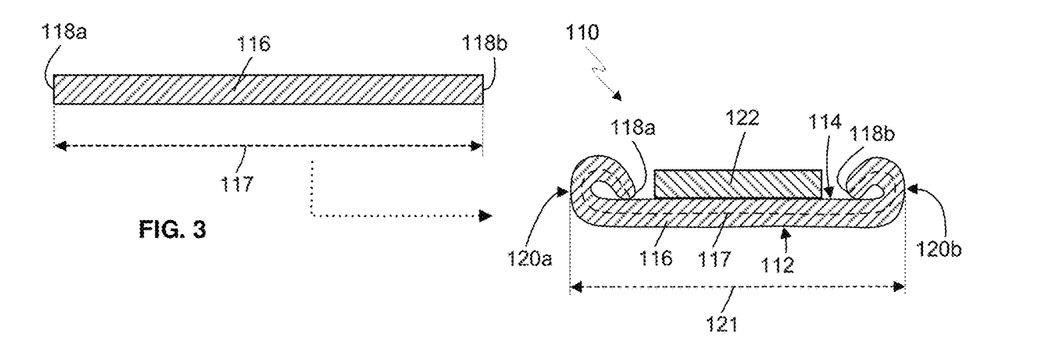
FIG. 3 is a sectional view of a hemostasis band according to another embodiment of the present disclosure, taken along a hypothetical section line similar to section line X-X of FIG. 1.

The inventors have discovered that attachments straps for hemostatic devices that include side (i.e., outer) edges that roll or curl away from the patient's limb provide improved patient comfort as compared to attachment straps having side edges that are planar with the remainder of the interior side of the attachment straps. FIG. 3 shows a sectional view of a piece 116 of material and a sectional view of an attachment strap 110 for a hemostasis band according to the present disclosure, which has been formed by rolling and heat-forming the side edges 118a,118b of the piece 116. Thus, the piece 116 has a width 117 (measured approximately along a centerline of its height), and the formed attachment strap 110 has a width 121 measured between side edges 120a,120b thereof, and the width 121 of the formed attachment strap 110 is less than the width 117 of the unformed piece 116. Further, the attachment strap 110 according to this embodiment comprises an interior side 112 that is oriented towards (i.e., faces) the wrist 3 and an exterior side 114 that is oriented away from the wrist 3 when the respective hemostatic device is attached thereto, with a fastener half 122 attached to the exterior side 114. In this embodiment, the interior side 112 of the attachment strap 110 is non-planar along the side edges 120a,120b with respect to the remainder of the interior side 112 when the respective hemostatic device is not attached around the patient's limb (or otherwise subject to outside forces or non-typical deformations, e.g., accidental or intentional plastic deformations of the piece 116). In this embodiment, the side edges 118a,118b of the piece 116 have not been surface-bonded to the exterior side 114 to form the attachment strap 110.

Figure 4:
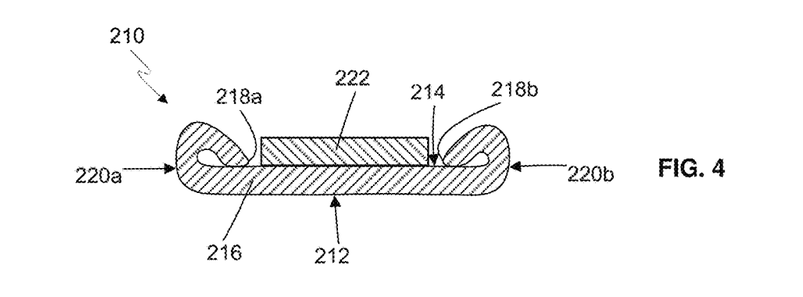
FIG. 4 is a sectional view of a hemostasis band according to another embodiment of the present disclosure, taken along a hypothetical section line similar to section line X-X of FIG. 1.

FIG. 4 shows a sectional view of another embodiment of an attachment strap 210 for a hemostasis band according to the present disclosure. In this embodiment, the attachment strap 210 has been formed from a piece 216 of material which has been formed by rolling and surface bonding the side edges 218a,218b of the piece 216 to an exterior side 214 of the piece 216 that is oriented away from the wrist 3 when the respective hemostatic device is attached thereto. Similar to the embodiment of FIG. 3, above, the formed attachment strap 210 has a width (not labeled) measured between side edges 220a,220b thereof that is less than a width (not labeled) of the unformed piece 216. An interior side 212 of the attachment strap 210 is oriented towards (i.e., faces) the wrist 3 when the respective hemostatic device is attached thereto, and a fastener half 222 is attached to the exterior side 214. In this embodiment, the interior side 212 of the attachment strap 210 is non-planar along the side edges 220a,220b with respect to the remainder of the interior side 212 when the respective hemostatic device is not attached around the patient's limb (or otherwise subject to outside forces or non-typical deformations, e.g., accidental or intentional plastic deformations of the piece 216). In alternate embodiments, instead of being surface bonded to the exterior side 214 of the piece 216, the side edges 218a,218b could be attached to the exterior side 214 of the piece 216 via heat sealing, ultrasonic welding, radio frequency welding, or a suitable adhesive or solvent.

Figure 5:
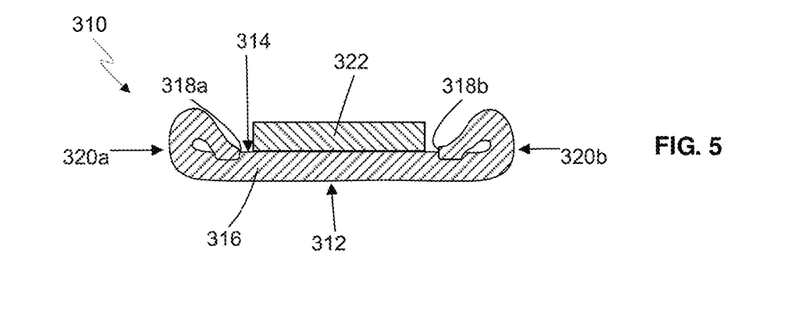
FIG. 5 is a sectional view of a hemostasis band according to another embodiment of the present disclosure, taken along a hypothetical section line similar to section line X-X of FIG. 1.

FIG. 5 shows a sectional view of another embodiment of an attachment strap 310 for a hemostasis band according to the present disclosure. In this embodiment, the attachment strap 310 has been formed from a piece 316 of material which has been formed by rolling and thermally bonding the side edges 318a,318b of the piece 316 to an exterior side 312 of the piece 316 that is oriented away from the wrist 3 when the respective hemostatic device is attached thereto. Similar to the embodiments of FIGS. 3 and 4, above, the formed attachment strap 310 has a width (not labeled) measured between side edges 320a,320b thereof that is less than a width (not labeled) of the unformed piece 316. An interior side 312 of the attachment strap 310 is oriented towards (i.e., faces) the wrist 3 when the attachment strap 310 is attached thereto, and a fastener half 322 is attached to the exterior side 314. In this embodiment, the interior side 312 of the attachment strap 310 is non-planar along the side edges 320a,320b with respect to the remainder of the interior side 312 when the respective hemostatic device is not attached around the patient's limb (or otherwise subject to outside forces or non-typical deformations, e.g., accidental or intentional plastic deformations of the piece 316).

Figure 6:
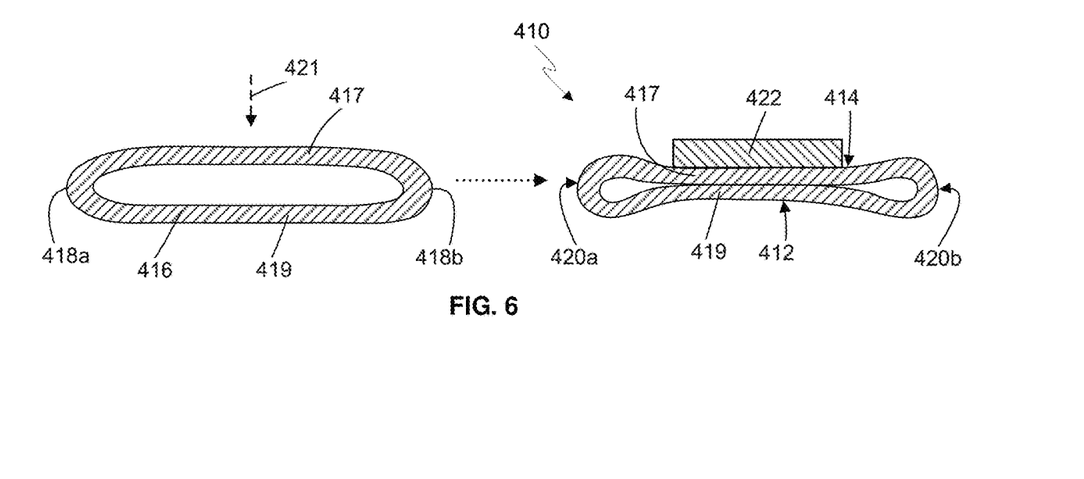
FIG. 6 is a sectional view of a hemostasis band according to another embodiment of the present disclosure, taken along a hypothetical section line similar to section line X-X of FIG. 1, in both an unassembled state and an assembled state.

FIG. 6 shows a sectional view of a piece 416 of material in a tubular shape having two halves 417,419 connected by two side edges 418a,418b, and a sectional view of an attachment strap 410 for a hemostasis band according to the present disclosure, which has been formed by pressing the two halves 417,419 of the piece 416 together in direction 421 and bonding them together such that the side edges 420a,420b of the attachment strap 410 are rounded. In this embodiment, the width (not labeled) of the piece 416—as measured between the side edges 418a,418b in an uncompressed state—is approximately the same as the width (not labeled) of the formed attachment strap 410 as measured between its side edges 420a,420b, after pressing and bonding. The attachment strap 410 according to this embodiment comprises an interior side 412 that is oriented towards (i.e., faces) the wrist 3 and an exterior side 414 that is oriented away from the wrist 3 when the respective hemostatic device is attached thereto, with a fastener half 422 attached to the exterior side 414. In this embodiment, the interior side 412 of the attachment strap 410 is non-planar along the side edges 420a,420b with respect to the remainder of the interior side 412 when the respective hemostatic device is not attached around the patient's limb (or otherwise subject to outside forces or non-typical deformations, e.g., accidental or intentional plastic deformations of the piece 416).

Figure 7:
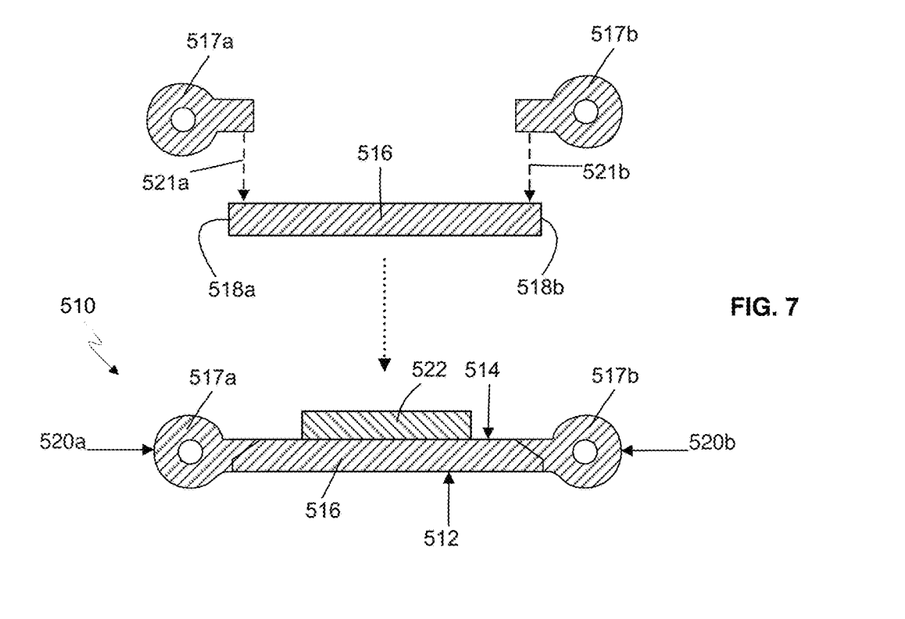
FIG. 7 is a sectional view of a hemostasis band according to another embodiment of the present disclosure, taken along a hypothetical section line similar to section line X-X of FIG. 1, in both an unassembled state and an assembled state.

FIG. 7 shows a sectional view of a primary piece 516 of material in a flat, planar shape and a pair of secondary pieces 517a,517b—which are formed with a rounded, extruded cross-sectional profile—and also a sectional view of an attachment strap 510 for a hemostasis band according to the present disclosure, which has been formed by pressing the two secondary pieces 517a,517b down in respective directions 521a,521b onto the primary piece 516 and bonding or otherwise attaching them thereto through any of the methods noted above. In this embodiment, the formed attachment strap 510 has a width (not labeled) measured between side edges 520a,520b thereof that is greater than a width (not labeled) of the unformed primary piece 516, as measured between its side edges 518a,518b. The interior side 512 of the attachment strap 510 is oriented towards (i.e., faces) the wrist 3 when the respective hemostatic device is attached thereto, and a fastener half 522 is attached to an exterior side 514 that is oriented away from the wrist 3 when the respective hemostatic device is attached thereto. In this embodiment, the interior side 512 of the attachment strap 510 is non-planar along the side edges 520a,520b with respect to the remainder of the interior side 512 when the respective hemostatic device is not attached around the patient's limb (or otherwise subject to outside forces or non-typical deformations, e.g., accidental or intentional plastic deformations of the pieces 516,517a,517b).

It should be understood that any of the attachment straps 110, 210, 310, 410, 510 according to the embodiments shown in FIGS. 3-7 could be attached to a main body and a compression element similar to the main body 32 and compression element 41 of the embodiment of FIG. 1, or similar to other known or not-yet-developed hemostatic devices.

FIGS. 8-11 show various views of another embodiment of a hemostasis band 610 according to the present disclosure, including attachment straps 614,632 that include edges that curl to the exterior of the band 610 (i.e., away from the patient) around at least a portion of a respective perimeter 622,640 thereof. It should be understood that the hemostasis band 610 according to the present disclosure include a main body 611 and a compression element (not shown or labeled) that may be similar to the main body 32 and compression element 41 of the embodiment of FIG. 1, or similar to other known or not-yet-developed hemostatic devices.

Figure 8:
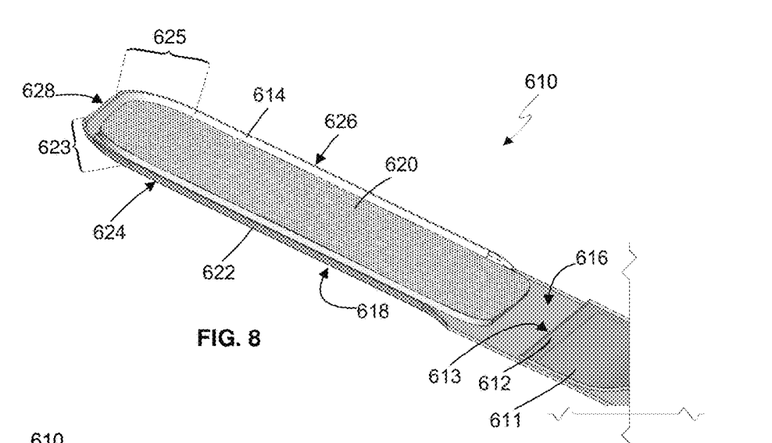
FIG. 8 is a side perspective view of a first end of a hemostasis band according to another embodiment of the present disclosure.
Figure 9:
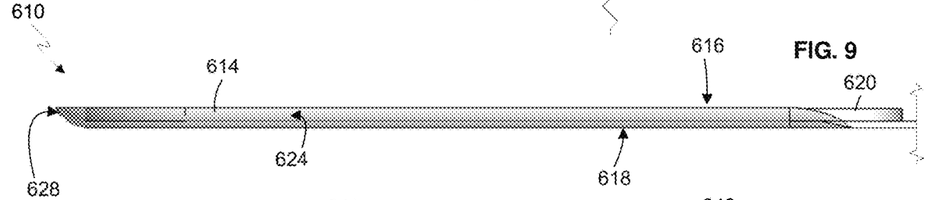
FIG. 9 is a side view thereof.

FIGS. 8 and 9 show perspective and side views, respectively, of the attachment strap 614 of the hemostasis band 610. The attachment strap 614 is attached to a main body 611 of the hemostasis band 610 by a flexible connector 612. The attachment strap 614 comprises an exterior side 616 which includes a fastener half 620 located thereon, an interior side 618, and the perimeter 622. The perimeter 622 is measured along a lateral edge 613 of the flexible connector 612 and along a side edge 624, an end edge 628, and a side edge 626 of the attachment strap 614 between a first point (not labeled) where the side edge 624 meets the flexible connector 612 and a second point (not labeled) where the side edge 626 meets the flexible connector 612, the lateral edge 613 of the flexible connector 612 being defined by a line drawn between the first point and the second point, and the end edge 628 including a corner 623 corresponding to where the end edge 628 meets the side edge 624 and a corner 625 corresponding to where the end edge 628 meets the side edge 626. In this embodiment, a majority of the linear length of the perimeter 622 of the attachment strap 614 includes an edge that curls outwardly towards the exterior side 616 (i.e., away from the patient's limb when worn). In this embodiment, a majority of the respective linear length of each of the side edges 624,626 and the entirety of the linear length of the end edge 628 (i.e., those respective portions of the perimeter 622 that correspond to each of the side edges 624,626 and end edge 628) include edges that curl outwardly towards the exterior side 616.

Figures 10, 11:
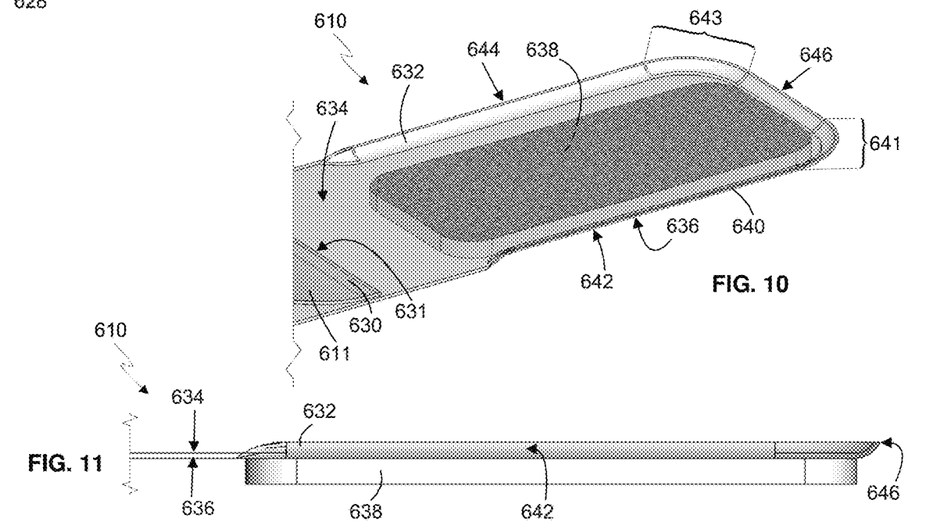
FIG. 10 is a side perspective view of a second end of the hemostasis band of FIG. 8.
FIG. 11 is a side view thereof.

FIGS. 10 and 11 show perspective and side views, respectively, of the attachment strap 632 of the hemostasis band 610. The attachment strap 632 is attached to the main body 611 of the hemostasis band 610 by a flexible connector 630. The attachment strap 632 comprises an exterior side 634, an interior side 636 which includes a fastener half 638 located thereon, and the perimeter 640. The perimeter 640 is measured along a lateral edge 631 of the flexible connector 630 and along a side edge 642, an end edge 646, and a side edge 644 of the attachment strap 632 between a first point (not labeled) where the side edge 642 meets the flexible connector 630 and a second point (not labeled) where the side edge 644 meets the flexible connector 630, the lateral edge 631 of the flexible connector 630 being defined by a line drawn between the first point and the second point, and the end edge 646 including a corner 641 corresponding to where the end edge 646 meets the side edge 642 and a corner 643 corresponding to where the end edge 646 meets the side edge 644. In this embodiment, a majority of the linear length of the perimeter 640 of the attachment strap 632 includes an edge that curls outwardly towards the exterior side 634 (i.e., away from the patient's limb when worn). In this embodiment, a majority of each of the respective linear length of each of the side edges 642,644 and the entirety of the linear length of the end edge 646 (i.e., those respective portions of the perimeter 640 that correspond to each of the side edges 642,644 and end edge 646) include edges that curl outwardly towards the exterior side 634.

As with the embodiment of FIG. 1, in the present embodiment the fastener halves 620,638 are releasably attachable together so that the attachment straps 614,632 are releasably attachable together to hold the hemostasis band 610 in place around the patient's wrist 3. Further, in the present embodiment, the corners 623,625, 641, 643 are each rounded (i.e., have a radius) for increased patient comfort. In alternate embodiments, any one or more of the corners 623, 625, 641, 643 could be chamfered, otherwise beveled, or could form a right angle.

In alternate embodiments according to the foregoing: at least 50% of the linear length of one or both side edges of an attachment strap could include an outwardly curled edge; at least 75% of the linear length of one or both side edges of an attachment strap could include an outwardly curled edge; and/or any percentage of the linear length of an end edge of an attachment strap could include an outwardly curled edge, for example 0%, more or less than 50%, or 100% thereof, including where the corner portions of the end edge include curled edges but the straight portion of the end edge does not, and vice-versa.

When the interior sides 618,636 of the respective attachment straps 614,632 of the hemostasis band 610 of the present disclosure are pressed against the user's wrist 3, the stresses applied to the wrist 3 by the hemostasis band 610 are spread out over side edges 624, 626, 642, 644, which each have a significantly wider surface area and a gentler edge transition than the sharp interior edge surfaces of the prior art embodiment shown in FIG. 2. Generally, the rolled and curled edges of the various embodiments shown in FIGS. 3-11 also act to distribute the stresses caused by the hemostatic devices across a wider area of the patient's wrist 3, thus improving the patient's comfort. Since the "hook" half of a hook-and-loop type fastener is typically considerably rougher than the "loop" half thereof, in each of the embodiments shown herein the patch of "loops" of the hook-and-loop fastener is preferably placed on the limb-facing side of the attachment strap in case this fastener half engages with the patient's skin, and the patch of "hooks" is preferably placed oriented facing away from the patient's skin when the attachment strap is in use, to minimize skin irritation caused by the fastener halves. In alternate embodiments, this arrangement could be reversed. Finally, it should be understood that any of the comfort-improving features disclosed herein could be combined, mutatis mutandis, in alternate embodiments according to the present disclosure.

While the principles of the claimed invention have been described above in connection with specific embodiment(s), it is to be clearly understood that this description is made only by way of example and not as a limitation of the scope of the invention, as set forth in the appended claims.

The invention claimed is:

1. A hemostatic device comprising:
a main body adapted to fit around at least a portion of a limb of a patient, at least one compression element connected to the main body and adapted to apply pressure to at least one artery or vein located in the limb when the hemostatic device is attached around the at least a portion of the limb;
a first attachment strap hingedly attached to the main body by a first flexible connector, the first attachment strap including a first fastener half, an interior side, an exterior side, and a perimeter, the perimeter being measured along a lateral edge of the first flexible connector and along a first side edge, an end edge, and a second side edge of the first attachment strap between a first point where the first side edge meets the first flexible connector and a second point where the second side edge meets the first flexible connector, the lateral edge of the first flexible connector being defined by a line drawn between the first point and the second point, the end edge including a first corner corresponding to where the end edge meets the first side edge and a second corner corresponding to where the end edge meets the second side edge; and
a second attachment strap hingedly attached to the main body by a second flexible connector, the second attachment strap including a second fastener half that is attachable to the first fastener half such that the first attachment strap and the second attachment strap are attachable together to hold the hemostatic device in place around the at least a portion of the limb, the second attachment strap further including an exterior side, an interior side and a perimeter, the perimeter of the second attachment strap being measured along a lateral edge of the second flexible connector and along a first side edge, an end edge, and a second side edge of the second attachment strap between a first point where the first side edge of the second attachment strap meets the second flexible connector and a second point where the second side edge of the second attachment strap meets the second flexible connector, the lateral edge of the second flexible connector being defined by a line drawn between the first point on the second attachment strap and the second point on the second attachment strap, the end edge of the second attachment strap including a first corner corresponding to where the end edge of the second attachment strap meets the first side edge thereof and a second corner corresponding to where the end edge of the second attachment strap meets the second side edge thereof;

the at least one compression element being located entirely between the first flexible connector and the second flexible connector as viewed from a top of the hemostatic device with the first and second attachment straps extending away from the main body;

wherein each of the interior sides of the first attachment strap and the second attachment strap is bounded by its respective perimeter, and each of the interior sides of the first attachment strap and the second attachment strap is oriented towards the at least a portion of the limb when the hemostatic device is attached around the at least a portion of the limb; and wherein at least one of the interior side of the first attachment strap and the interior side of the second attachment strap is non-planar when the hemostatic device is not attached around the at least a portion of the limb, the first attachment strap being made of a material so that the first and second side edges of the first attachment strap as well as the exterior side of the first attachment strap are constituted by said material, the second attachment strap being made of said material so that the first and second side edges of the second attachment strap as well as the exterior side of the second attachment strap are constituted by said material, wherein at least one of the first side edge of the first attachment strap, the second side edge of the first attachment strap, the first side edge of the second attachment strap, and the second side edge of the second attachment strap is rolled or curled away from the interior side of the respective attachment strap, with a surface of the respective attachment strap that extends between the exterior and interior sides of the respective attachment strap being directly in contact with and bonded to the exterior side of the respective attachment strap so that the respective attachment strap is folded-over onto itself and is bonded to itself, and said material constituting the at least one of the first side edge of the first attachment strap, the second side edge of the first attachment strap, the first side edge of the second attachment strap, and the second side edge of the second attachment strap is directly bonded to said material constituting the exterior side of the respective attachment strap.

2. The hemostatic device of claim 1, wherein at least one of the first side edge of the first attachment strap, the second side edge of the first attachment strap, the first side edge of the second attachment strap, and the second side edge of the second attachment strap includes at least one cutout.

3. The hemostatic device of claim 2, wherein at least one of the first side edge of the first attachment strap, the second side edge of the first attachment strap, the first side edge of the second attachment strap, and the second side edge of the second attachment strap includes a plurality of cutouts.

4. The hemostatic device of claim 2, wherein each of the first side edge of the first attachment strap, the second side edge of the first attachment strap, the first side edge of the second attachment strap, and the second side edge of the second attachment strap includes at least one cutout.

5. The hemostatic device of claim 1, wherein at least one of the first attachment strap and the second attachment strap is comprised of a piece of material having a width that is greater than a width of the respective attachment strap when the respective attachment strap is in an unformed state, wherein the widths are measured in a direction that is orthogonal to a longitudinal length of either of the respective side edges of the respective attachment strap.

6. The hemostatic device of claim 1, wherein at least one of the first attachment strap and the second attachment strap is comprised of a primary piece of material and at least one secondary piece of material that is attached to the primary piece of material to form at least a portion of the first side edge or second side edge of the respective attachment strap, the at least one secondary piece of material being rolled or curled away from the interior side of the respective attachment strap.

7. The hemostatic device of claim 1, wherein at least one of the first corner or the second corner of the end edge of the first attachment strap or the first corner or the second corner of the end edge of the second attachment strap is rounded or chamfered.

8. The hemostatic device of claim 1, the main body further comprising a curved plate that wraps around the at least a portion of the limb when the hemostatic device is attached around the at least a portion of the limb, wherein at least a portion of the at least one compression element is located between the curved plate and the at least one artery or vein.

9. The hemostatic device of claim 8, the curved plate being more rigid than the first attachment strap and the second attachment strap.

10. The hemostatic device of claim 1, wherein the at least one compression element comprises at least one inflatable element.

11. The hemostatic device of claim 10, wherein the at least one compression element comprises a plurality of inflatable elements that press into each other when inflated to assist in the application of pressure to the at least one artery or vein.

12. A hemostatic device comprising:
a main body adapted to fit around at least a portion of a limb of a patient, and at least one inflatable compression element that is inflatable to apply pressure to at least one artery or vein located in the limb when the hemostatic device is attached around the at least a portion of the limb, the at least one inflatable compression element being connected to the main body by a connector;
a first attachment strap hingedly attached to the main body by a first flexible connector, the first attachment strap including a first fastener half, an interior side bounded by a perimeter, and an exterior side, the first fastener half being attached to the exterior side of the first attachment strap, the perimeter being measured along a first side edge, an end edge, and a second side edge of the first attachment strap between a first point where the first side edge meets the first flexible connector and a second point where the second side edge meets the first flexible connector; and a second attachment strap hingedly attached to the main body by a second flexible connector, the second attachment strap including a second fastener half that is attachable to the first fastener half such that the first attachment strap and second attachment strap are attachable together to hold the hemostatic device in place around the at least a portion of the limb, the second attachment strap further including an interior side bounded by a perimeter, and an exterior side, the second fastener half being attached to the interior side of the second attachment strap, the perimeter of the second attachment strap being measured along a first side edge, an end edge, and a second side edge of the second attachment strap between a first point where the first side edge of the second attachment strap meets the second flexible connector and a second point where the second side edge of the second attachment strap meets the second flexible connector;

the at least one compression element being located entirely between the first side edge of the first attachment strap and the first side edge of the second attachment strap as viewed from a top of the hemostatic device with the first and second attachment straps extending away from the main body;

the connector being located between the first side edge of the first attachment strap and the first side edge of the second attachment strap as viewed from the top of the hemostatic device with the first and second attachment straps extending away from the main body;

the first attachment strap being made of a material so that the first and second side edges of the first attachment strap as well as the exterior side of the first attachment strap are constituted by said material;

wherein each of the interior sides of the first attachment strap and the second attachment strap is oriented towards the at least a portion of the limb when the hemostatic device is attached around the at least a portion of the limb;

wherein at least one of the interior side of the first attachment strap and the interior side of the second attachment strap is non-planar when the hemostatic device is not attached around the at least a portion of the limb; and wherein the first side edge of the first attachment strap and the second side edge of the first attachment strap are rolled or curled away from the interior side of the first attachment strap, with a surface of the first attachment strap that extends between the exterior and interior sides of the first attachment strap being directly in contact with and bonded to the exterior side of the first attachment strap so that said material constituting the first and second side edges of the first attachment strap is directly bonded to said material constituting the exterior side of the respective attachment strap.

13. A hemostatic device comprising:

a main body adapted to fit around at least a portion of a limb of a patient, at least one compression element connected to the main body and configured to apply pressure to at least one artery or vein located in the limb when the main body is fitted around the at least a portion of the limb, the main body including one end and an other end that are spaced apart from one another along a longitudinal extent of the main body, the main body also including oppositely disposed first and second side edges that extend along the longitudinal extent of the main body, the first side edge of the main body being linear along its entire longitudinal extent, the second side edge of the main body being linear along its entire longitudinal extent;

a first attachment strap hingedly attached to the one end of the main body by a first flexible connector, the first attachment strap including an interior side configured to face towards the at least a portion of the limb when the hemostatic device is fitted around the at least a portion of the limb, an exterior side configured to face away from the at least a portion of the limb when the hemostatic device is fitted around the at least a portion of the limb, a first fastener half on the interior side or the exterior side of the first attachment strap, and a perimeter, the perimeter being measured along a lateral edge of the first flexible connector and along a first side edge, an end edge, and a second side edge of the first attachment strap between a first point where the first side edge of the first attachment strap meets the first flexible connector and a second point where the second side edge of the first attachment strap meets the first flexible connector, the lateral edge of the first flexible connector being defined by a line drawn between the first point and the second point, the end edge of the first attachment strap including a first corner corresponding to where the end edge of the first attachment strap meets the first side edge of the first attachment strap and a second corner corresponding to where the end edge of the first attachment strap meets the second side edge of the first attachment strap;

a second attachment strap hingedly attached to the other end of the main body by a second flexible connector, the second attachment strap including an interior side configured to face towards the at least a portion of the limb when the hemostatic device is fitted around the at least a portion of the limb, an exterior side configured to face away from the at least a portion of the limb when the hemostatic device is fitted around the at least a portion of the limb, a second fastener half on the interior side or the exterior side of the second attachment strap, the second fastener half being configured to be attached to the first fastener half such that the first attachment strap and second attachment strap are attachable together to hold the hemostatic device in place around the at least a portion of the limb and to permit size adjustment of the first and second attachment straps to accommodate different size limbs, the second attachment strap further including a perimeter, the perimeter of the second attachment strap being measured along a lateral edge of the second flexible connector and along a first side edge, an end edge, and a second side edge of the second attachment strap between a first point where the first side edge of the second attachment strap meets the second flexible connector and a second point where the second side edge of the second attachment strap meets the second flexible connector, the lateral edge of the second flexible connector being defined by a line drawn between the first point on the second attachment strap and the second point on the second attachment strap, the end edge of the second attachment strap including a first corner corresponding to where the end edge of the second attachment strap meets the first side edge thereof and a second corner corresponding to where the end edge of the second attachment strap meets the second side edge thereof;

at least one of the first side edge of the first attachment strap, the second side edge of the first attachment strap, the first side edge of the second attachment strap, and the second side edge of the second attachment strap being non-linear to interrupt and reduce tension applied to the limb of the patient and being different from the first fastener half and the second fastener halt;

the first side edge of the first attachment strap and the second side edge of the first attachment strap being non-linear, the first side edge of the first attachment strap including a first cut-out portion defining the non-linearity of the first side edge of the first attachment strap, the second side edge of the first attachment strap including a second cut-out portion defining the non-linearity of the second side edge of the first attachment strap; and the first side edge of the first attachment strap including linear portions on opposite sides of the first cut-out portion, the linear portions on opposite sides of the first cut-out portion having a greater length along the longitudinal extent of the main body than the first cut-out portion, the second side edge of the first attachment strap including linear portions on opposite sides of the second cut-out portion, the linear portions on opposite sides of the second cut-out portion having a greater length along the longitudinal extent of the main body than the second cut-out portion.

14. The hemostatic device of claim 13, wherein the first side edge of the second attachment strap and the second side edge of the second attachment strap are non-linear, the first side edge of the second attachment strap including a third cut-out portion defining the non-linearity of the first side edge of the second attachment strap, the second side edge of the second attachment strap including a fourth cut-out portion defining the non-linearity of the second side edge of the second attachment strap.

15. The hemostatic device of claim 14, wherein the first side edge of the second attachment strap includes linear portions on opposite sides of the third cut-out portion, the linear portions on opposite sides of the third cut-out portion having a greater length along the longitudinal extent of the main body than the third cut-out portion, the second side edge of the second attachment strap including linear portions on opposite sides of the fourth cut-out portion, the linear portions on opposite sides of the fourth cut-out portion having a greater length along the longitudinal extent of the main body than the fourth cut-out portion.

16. The hemostatic device of claim 13, wherein the first side edge of the first attachment strap and the second side edge of the first attachment strap are non-linear, and the first side edge of the second attachment strap and the second side edge of the second attachment strap are non-linear, the first side edge of the first attachment strap including plural first cut-out portions spaced apart along the longitudinal extent of the main body and defining the non-linearity of the first side edge of the first attachment strap, the second side edge of the first attachment strap including plural second cut-out portions spaced apart along the longitudinal extent of the main body and defining the non-linearity of the second side edge of the first attachment strap.

17. The hemostatic device of claim 16, wherein the first side edge of the first attachment strap includes linear portions on opposite sides of one of the plural first cut-out portions, the linear portions on opposite sides of the one of the plural first cut-out portions having a greater length along the longitudinal extent of the main body than the one of the plural first cut-out portions, the second side edge of the first attachment strap including linear portions on opposite sides of one of the plural second cut-out portions, the linear portions on opposite sides of the one of the plural second cut-out portions having a greater length along the longitudinal extent of the main body than the one of the plural second cut-out portions.

* * * * *